(12) United States Patent
Locarno et al.

(10) Patent No.: US 11,925,546 B2
(45) Date of Patent: Mar. 12, 2024

(54) SOFT TISSUE REPAIR AND METHODS FOR PREPARING SAME

(71) Applicant: Musculoskeletal Transplant Foundation, Edison, NJ (US)

(72) Inventors: Michael Locarno, Kinnelon, NJ (US); Bryan Choi, San Marcos, CA (US); Manh-Dan Ngo, Matawan, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 520 days.

(21) Appl. No.: 17/111,147

(22) Filed: Dec. 3, 2020

(65) Prior Publication Data

US 2021/0085448 A1 Mar. 25, 2021

Related U.S. Application Data

(60) Division of application No. 16/244,190, filed on Jan. 10, 2019, now Pat. No. 10,881,501, which is a division of application No. 15/621,602, filed on Jun. 13, 2017, now Pat. No. 10,238,485, which is a continuation of application No. 14/208,025, filed on Mar. 13, 2014, now abandoned.

(60) Provisional application No. 61/783,237, filed on Mar. 14, 2013.

(51) Int. Cl.
| | |
|---|---|
| *A61F 2/10* | (2006.01) |
| *A61K 35/36* | (2015.01) |
| *A61L 27/36* | (2006.01) |
| *A61L 27/38* | (2006.01) |
| *A61L 27/60* | (2006.01) |
| *C12N 5/071* | (2010.01) |

(52) U.S. Cl.
CPC .............. *A61F 2/105* (2013.01); *A61K 35/36* (2013.01); *A61L 27/362* (2013.01); *A61L 27/3683* (2013.01); *A61L 27/38* (2013.01); *A61L 27/60* (2013.01); *C12N 5/0698* (2013.01)

(58) Field of Classification Search
CPC ...... A61L 27/3683; A61L 27/60; A61L 27/38; A61L 27/362; C12N 5/0698; A61F 2/105; A61K 35/36
See application file for complete search history.

(56) References Cited

U.S. PATENT DOCUMENTS

| | | | |
|---|---|---|---|
| 4,776,853 | A | 10/1988 | Klement et al. |
| 6,497,875 | B1 | 12/2002 | Sorrell |
| 6,734,018 | B2 | 5/2004 | Wolfinbarger et al. |
| 7,358,284 | B2 | 4/2008 | Griffey |
| 7,582,309 | B2 | 9/2009 | Rosenberg |
| 7,723,108 | B2 | 5/2010 | Truncale et al. |
| 7,799,325 | B2 | 9/2010 | Kleinsek |
| 8,067,149 | B2 | 11/2011 | Livesey et al. |
| 8,425,600 | B2 | 4/2013 | Maxwell |
| 8,557,581 | B2 | 10/2013 | Ngo et al. |
| 8,986,377 | B2 | 3/2015 | Richter et al. |
| 9,162,011 | B2 | 10/2015 | Stillwell et al. |
| 9,206,442 | B2 | 12/2015 | Chen |
| 9,375,513 | B2 | 6/2016 | Sun et al. |
| 10,449,034 | B2 | 10/2019 | Bowley et al. |
| 10,835,370 | B2 | 11/2020 | Bowley et al. |
| 10,869,745 | B2 | 12/2020 | Lee et al. |
| 10,881,501 | B2 | 1/2021 | Locarno et al. |
| 10,959,833 | B2 | 3/2021 | Ansorge et al. |
| 2005/0186286 | A1 | 8/2005 | Takami |
| 2007/0207125 | A1 | 9/2007 | Bothwell et al. |
| 2007/0269791 | A1 | 11/2007 | Takami et al. |
| 2008/0097601 | A1 | 4/2008 | Codor-Hurff et al. |
| 2008/0154366 | A1 | 6/2008 | Frank |
| 2010/0112543 | A1 | 5/2010 | Ngo et al. |
| 2011/0022171 | A1 | 1/2011 | Richter et al. |
| 2011/0035004 | A1 | 2/2011 | Maxwell |
| 2012/0010728 | A1 | 1/2012 | Sun et al. |
| 2012/0034191 | A1 | 2/2012 | Matheny |
| 2012/0263763 | A1 | 10/2012 | Sun et al. |
| 2012/0276213 | A1 | 11/2012 | Chen |
| 2012/0329034 | A1 | 12/2012 | Chun et al. |
| 2013/0013068 | A1 | 1/2013 | Forsell et al. |
| 2013/0158658 | A1 | 6/2013 | Hayzlett |
| 2013/0287741 | A1 | 10/2013 | Stillwell et al. |
| 2015/0157451 | A1 | 6/2015 | Bowley |
| 2015/0223928 | A1 | 8/2015 | Limem |
| 2015/0250582 | A1 | 9/2015 | Greenhalgh |
| 2016/0199173 | A1 | 7/2016 | Liu |
| 2016/0367726 | A1 | 12/2016 | Gratzer |
| 2017/0367807 | A1 | 12/2017 | Chen et al. |
| 2020/0405473 | A1 | 12/2020 | Nanni |
| 2021/0015602 | A1 | 1/2021 | Bowley et al. |
| 2021/0022849 | A1 | 1/2021 | Barere et al. |
| 2021/0085443 | A1 | 3/2021 | Kocak et al. |

FOREIGN PATENT DOCUMENTS

| | | |
|---|---|---|
| EP | 3034038 | 6/2016 |
| WO | 1984004880 | 12/1984 |

(Continued)

OTHER PUBLICATIONS

Krejci et al. In Vitro Reconstitution of Skin: Fibroblasts Facilitate Keratinocyte Growth and Differentiation on Acellular Reticular Dermis. J Invest Dermatol 97: 843-848, 1991. (Year: 1991).*
Non-Final Office Action for U.S. Appl. No. 16/244,190, dated Apr. 17, 2020.
Office Action response dated Aug. 17, 2020 for Non-Final Office Action dated Apr. 17, 2020, for U.S. Appl. No. 16/244,190.

(Continued)

*Primary Examiner* — Sean C. Barron
(74) *Attorney, Agent, or Firm* — Marcella M. Bodner; Cole Schotz, P.C.

(57) ABSTRACT

Allografts for soft tissue repair, including breast reconstruction and other plastic surgery procedures, are disclosed. One allograft is made from decellularized dermal tissue and constitutes a collagen matrix having substantially uniform density and porosity. Another allograft is a hybrid bilayer tissue form that is made from decellularized dermal and adipose tissues. Methods for making both allografts are also disclosed.

16 Claims, 12 Drawing Sheets

(56) References Cited

FOREIGN PATENT DOCUMENTS

| WO | 2008154623 | 12/2008 |
|----|------------|---------|
| WO | 20080154623 | 12/2008 |
| WO | 2014160008 | 10/2014 |
| WO | 2015065923 | 5/2015 |

OTHER PUBLICATIONS

Notice of Allowance for U.S. Appl. No. 16/244,190, dated Oct. 14, 2020.
Issue Fee Payment Transmittal for U.S. Appl. No. 16/244,190, filed Dec. 3, 2020.
Butler et al. Reduction of Adhesions with Composite AlloDerm/Polypropylene Mesh Implants for Abdominal Wall Reconstruction. Plast. Reconstr. Surg.(2004), v114, p. 464-473.
Erdag, et al., "Fibroblasts Improve Performance of Cultured Composite Skin Substitutes on Athymic Mice", Burns, 30 (2004) pp. 322-328.
Final Office Action for U.S. Appl. No. 14/208,025, dated Aug. 19, 2016.
Final Office Action for U.S. Appl. No. 15/173,286, dated Jan. 26, 2018.
Final Office Action for U.S. Appl. No. 15/173,286, dated Nov. 25, 2019.
Final Office Action for U.S. Appl. No. 15/621,602, dated Nov. 13, 2017.
First Examination Report in related New Zealand Patent Application No. 710330, dated Feb. 25, 2016.
Further Examination Report in related New Zealand Patent Application No. 710330, dated Feb. 8, 2017.
Further Examination Report in related New Zealand Patent Application No. 710330, dated Oct. 11, 2016.
International Preliminary Report on Patentability for PCT/US2014/025619, dated Sep. 15, 2015.
International Search Report and Written Opinion for related International (PCT) Application No. PCT/US2014/025619, dated Jun. 30, 2014.
Isch et al. Patch Esophagoplasty Using AlloDerm as a Tissue Scaffold. Journal of Pediatric Surgery (2001 ), v36(2), p. 266-268.
Kesmarky G., et al., "Plasma viscosity: A forgotten variable", Clinical Hemorcheology and Microcirculation, 2008, vol. 39, pp. 243-246, IOS Press.
Kolker et al. Multilayer Reconstruction of Abdominal Wall Defects With Acellular Dermal Allograft (AlloDerm) and 3omponent Separation. Annals of Plastic Surgery (2005), v55(1 ), p. 36-42.
Leung et al. Skin Grafts. UTMJ (2009), v86(2), p. 61-64.
Li Y., et al., "Experimental validation of non-invasive and fluid density independent methods for the determination of local wave speed and arrival time of reflected wave", Journal of Biomechanics, 2011, vol. 44, pp. 1393-1399, Elsevier.
Mine et al. Aging Alters Functionally Human Dermal Papillary Fibroblasts but Not Reticular Fibroblasts: A New View of Skin Morphogenesis and Aging. PLoS One (2008), v3(12), e4066, 13 pages.
Mulder G. D., "Quantifying wound fluids for the clinician and researcher", Ostomy / Wound Management, 1994, vol. 40, pp. 65-69.
Non-Final Office Action for U.S. Appl. No. 15/173,286, dated Aug. 3, 2017.
Office Action for U.S. Appl. No. 14/208,025, dated Feb. 26, 2016.
Office Action for U.S. Appl. No. 14/208,025, dated Mar. 13, 2017.
Office Action for U.S. Appl. No. 15/173,286, dated Jul. 10, 2018.
Office Action for U.S. Appl. No. 15/621,602, dated Jul. 12, 2018.
Office Action for U.S. Appl. No. 15/621,602, dated Aug. 10, 2017.
Office Action for U.S. Appl. No. 15/858,360 dated May 11, 2018.
Office Action in related Canadian Patent Application No. 2,899,642, dated Oct. 24, 2017.
Office Action in related Canadian Patent Application No. 2,899,642, dated Sep. 13, 2016.
Office Action issued for related European Patent Application No. 14718250.5, dated Nov. 23, 2016.
Oliver, et al., "Reconstruction of Full-Thickness Loss Skin Wounds Using Skin Collagen Allografts", British Journal of Plastic Surgery, 32 (1979), pp. 87-90.
Ownby (2010). The Integument—the skin and all of it's derivatives.
Patent Examination Report No. 1 in related Australian Patent Application No. 2014244272, dated Mar. 10, 2016.
Patent Examination Report No. 1 in related Australian Patent Application No. 2016234904, dated Apr. 28, 2017.
Restriction Requirement for U.S. Appl. No. 14/208,025, dated Nov. 3, 2015.
Restriction Requirement for U.S. Appl. No. 15/915,412, dated May 14, 2020.
Shuster et al. The influence of age and sex on skin thickness, skin collagen and density. British Journal of Dermatology ;1975), v96, p. 639-643.
U.S. Appl. No. 15/915,412, filed Mar. 8, 2018.
Design U.S. Appl. No. 29/566,994, filed Jun. 3, 2016.
U.S. Appl. No. 15/032,567, filed Apr. 27, 2016.
U.S. Appl. No. 15/173,286, filed Jun. 3, 2016.
U.S. Appl. No. 14/208,025, filed Mar. 13, 2014.
U.S. Appl. No. 15/621,602, filed Jun. 13, 2017.
U.S. Appl. No. 15/858,360, filed Dec. 29, 2017.
U.S. Appl. No. 61/783,237, filed Mar. 14, 2013.
U.S. Appl. No. 62/440,526, filed Dec. 30, 2016.
U.S. Appl. No. 62/468,511, filed Mar. 8, 2017.
Issue Notification dated Dec. 16, 2020 for corresponding U.S. Appl. No. 16/244,190.

\* cited by examiner

FIG. 3
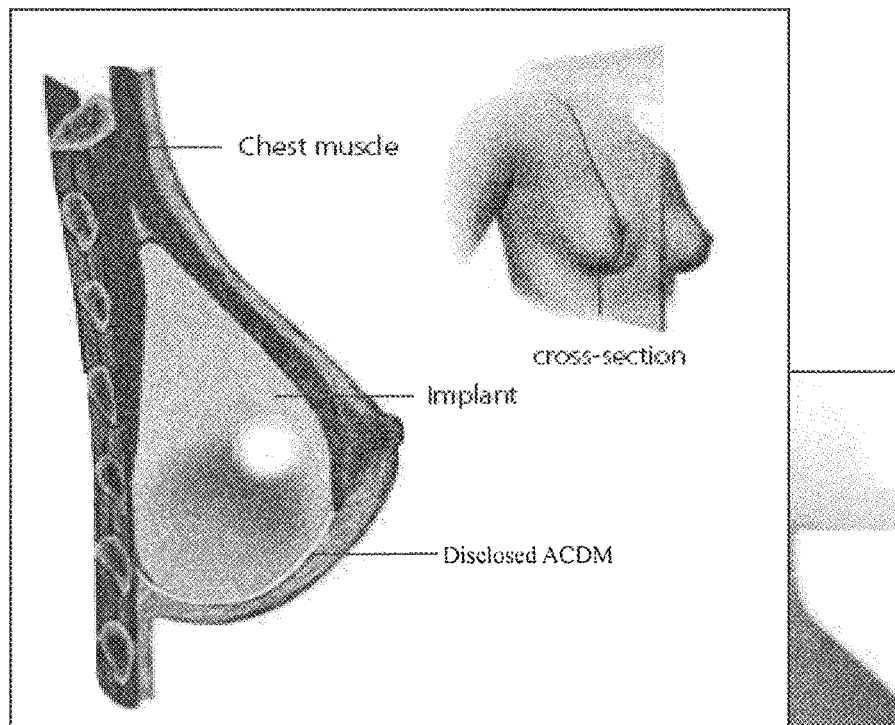
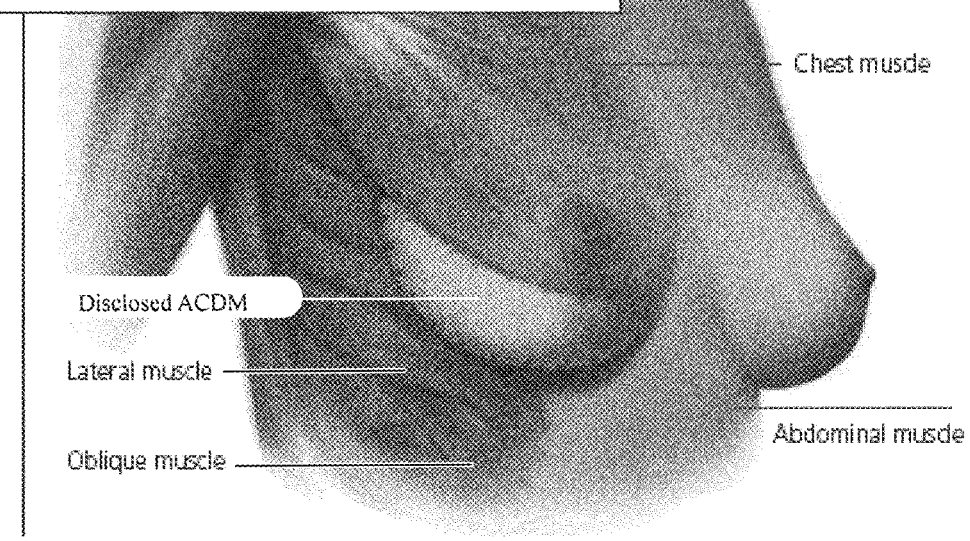
FIG. 4

*error is represented as standard error of the mean (SEM)

FlexHD Structural ACDM epidermal side          dermal side

Disclosed ACDM epidermal side          dermal side

FlexHD Structural ACDM

Disclosed ACDM

SOFT TISSUE REPAIR AND METHODS FOR PREPARING SAME

RELATED APPLICATIONS

This is a divisional of U.S. patent application Ser. No. 16/244,190, filed Jan. 10, 2019 and now allowed, which is a divisional of U.S. patent application Ser. No. 15/621,602, filed Jun. 13, 2017 and issued as U.S. Pat. No. 10,238,485 on Mar. 26, 2019, which is a continuation application of U.S. patent application Ser. No. 14/208,025, filed Mar. 13, 2014 and now abandoned, and claims the benefit of U.S. Provisional Patent Application No. 61/783,237, filed Mar. 14, 2013, the disclosures of each of which are incorporated in their entirety herein.

FIELD OF THE INVENTION

The present invention relates generally to allografts made from decellularized dermal tissues, and in particular, to the use of such allografts for soft tissue repair, including breast reconstruction and other plastic surgery procedures.

BACKGROUND OF THE INVENTION

Human allograft dermal tissue has been widely accepted for use in various surgical procedures for decades. For example, acellular dermal matrices ("ACDMs") derived from allograft dermal tissue are used in the repair of ventral abdominal hernias and other abdominal wall defects. Commercially available ACDMs include FlexHD® Structural™ ACDM, which is marketed by Musculoskeletal Transplant Foundation (Edison, N.J.), as well as AlloDerm® ACDM and AlloDerm® Ready to Use ("RTU") ACDM, both of which are marketed by LifeCell Corporation (Branchburg, N.J.). The nature of the dermal tissue from which these ACDMs are derived is explained with reference to FIG. 1, which illustrates the microstructure of human skin.

Human allograft skin, as illustrated in FIG. 1, is recovered from either live or deceased donors after receiving consent from the individual donor or donor's family. The skin is made of several layer-like components, including the outermost epidermis E, and the dermis D, which lies beneath the epidermis. The hypodermis H (also referred to as the subcutis) lies beneath the dermis D, but is not part of the skin. Rather, the hypodermis H contains adipose and muscle tissue. The dermis D itself includes the papillary dermis PD, which lies adjacent the epidermis E, and the reticular dermis RD, which lies between the papillary dermis PD and the hypodermis H. The papillary-reticular dermis interface PRI, lies between the papillary dermis PD and the reticular dermis RD. The dermis-epidermis junction ("the DEJ") lies between the papillary dermis PD and epidermis E.

The process for deriving the foregoing ACDMs from dermal tissue involves removing the epidermis E (e.g., by a chemical process that causes the epidermis to slough off), and thereby exposing the DEJ that was adjacent the epidermis E. Beneath the DEJ lies the papillary dermis PD, the papillary-reticular dermal interface PRI, and the reticular dermis RD. The dermal tissue that is recovered for the ACDMs may therefore include the DEJ, papillary dermis PD and at least part of the reticular dermis RD. The recovered dermal tissue is decellularized and aseptically processed to meet sterility testing requirements.

The foregoing ACDMs are derived from recovered tissue that includes the entire papillary dermis PD. The microstructure of the papillary dermis PD is not uniform. More particularly, the papillary dermis PD has an upper portion, or side, that was immediately adjacent the DEJ and therefore closer to the epidermis E (i.e., "the epidermal portion"), and a structurally different lower portion, or side, that was farther from the DEJ and epidermis E, and adjacent the deeper reticular dermis RD (i.e., "the dermal portion"). The epidermal portion of the papillary dermis PD contains a more densely-packed collagen matrix than the relatively more open collagen matrix contained in the dermal portion. As such, the dermal portion is more porous than the epidermal portion. This dual structure is also a property of the foregoing ACDMs, and is ideal for repairing ventral abdominal hernias and other abdominal wall defects, as the more densely-packed epidermal portion of the ACDM (i.e., incorporating the epidermal portion of the papillary dermis PD) possesses the tensile strength and stiffness required for such load-bearing tissue repairs, and the more porous dermal portion of the ACDM (i.e., incorporating the dermal portion of the papillary dermis PD, as well as at least a portion of the loosely-packed and porous underlying reticular dermis RD) provides an open collagen structure that promotes vascularization, cellular attachment and tissue ingrowth. Nevertheless, this dual structure, which may only be visible on a microscopic scale, presents concerns about identifying and maintaining the side orientation of the ACDM, i.e., during a surgical procedure.

Allograft dermal tissue-derived ACDMs have also been used in plastic surgery procedures, including breast reconstruction, where the ACDM is implanted to function as an internal sling that is draped around a breast implant and/or tissue expander. While the high tensile strength and stiffness of the foregoing ACDMs are important for hernia and abdominal wall repairs, breast reconstruction and other plastic surgery procedures do not involve the load-bearing and other tissue considerations inherent in hernia and abdominal wall repairs. Instead, materials used as slings and similar devices in breast reconstruction should possess biomechanical properties that are well-suited to such applications, including predictable suppleness, flexibility and uniform pliability sufficient for such slings to stretch and expand without tearing during tissue expansion (i.e., using breast implant and/or tissue expander). Ideal materials for breast reconstruction and other plastic surgery procedures should also possess sufficient tensile strength, preclude suture tear-out, both during implantation and expansion through the post-operative phase, and allow rapid and efficient cellular ingrowth equally from either side of the ACDM.

SUMMARY OF THE INVENTION

The present invention relates to a soft tissue repair allograft, and more particularly to an allograft dermal tissue-derived ACDM, and its use in plastic surgery procedures, including breast reconstruction. The ACDM of the present invention is derived from deeper-cut dermal tissue, which constitutes a collagen matrix having substantially uniform density and porosity, and therefore possesses the foregoing structural and biomechanical properties that make it well-suited for use in breast reconstruction procedures, e.g., as a sling, as well as other plastic surgery applications. The allograft dermal tissue form, or ACDM, includes a portion of dermal tissue having a first exposed surface formed by a first cut and a second exposed surface formed by a second cut opposite the first exposed surface, wherein the portion of dermal tissue constitutes a collagen matrix having substantially uniform density and porosity between the first and second exposed surfaces.

The present invention also relates to a method for preparing an ACDM, i.e., an allograft dermal tissue form, from donor tissue. The method involves (1) making a first cut into the reticular dermis RD at a first location distal the papillary-reticular dermis interface PRI, and along a first plane substantially parallel to the papillary-reticular dermis interface PRI; (2) removing the hypodermis H from the reticular dermis RD along the first cut to form a first exposed surface on a remaining portion of the donor tissue; (3) making a second cut into the papillary dermis PD at a second location proximate the DEJ, and along a second plane substantially parallel to the papillary-reticular dermis interface PRI and the first plane; and (4) removing the epidermis E, DEJ and a portion of the papillary dermis PD from the remaining portion of the donor tissue to form a second exposed surface on a remaining portion of the dermis D opposite the first exposed surface. The first and second locations are selected such that the remaining portion of the dermis D constitutes a collagen matrix having substantially uniform density and porosity between the first exposed surface and the second exposed surface.

The present invention further relates to an allograft hybrid bilayer tissue form having a dermal side and an adipose side for use in surgical procedures, as well as a method for forming the allograft hybrid bilayer tissue form. The method involves (1) providing donor tissue including skin having (a) an epidermis E and (b) a dermis D underlying the epidermis E, the dermis D including a papillary dermis PD adjacent the epidermis E, a reticular dermis RD distal to the epidermis E, and a papillary-reticular dermis interface PRI between the papillary dermis PD and reticular dermis RD; and a hypodermis H adipose tissue underlying the reticular dermis RD; (2) making a cut into the reticular dermis RD at a location proximate the hypodermis H, and along a plane substantially parallel to the papillary-reticular dermis interface PRI; and (3) removing the hypodermis H and a portion of the reticular dermis RD attached to the hypodermis H to form the allograft hybrid bilayer tissue form such that the allograft hybrid bilayer tissue form includes both a dermal side and an adipose side.

BRIEF DESCRIPTION OF THE DRAWINGS

The present invention will be further explained with reference to the attached drawings, wherein like structures are referred to by like numerals and/or letters throughout the several views. The drawings shown are not necessarily to scale, with emphasis instead generally being placed upon illustrating the principles of the present invention.

FIG. 3 is a cross-sectional schematic view of an ACDM being used as a sling for breast reconstruction according to an embodiment of the present invention;

FIG. 4 is a perspective view of an ACDM being used as a sling for breast reconstruction according to an embodiment of the present invention;

DETAILED DESCRIPTION OF THE INVENTION

Detailed embodiments of the present invention are disclosed herein. It should be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, and some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as examples for teaching one skilled in the art to variously employ the present invention.

The present invention generally relates to dermal allografts for use in the repair of soft tissue defects. More particularly, the present invention relates to a flexible, pliable acellular dermis surgical implant, or tissue form, comprising a section cut from a full thickness dermal tissue. The ACDMs of the present invention possess structural and biomechanical properties that are conducive to their use in breast reconstruction and other plastic surgery applications. Such properties include, but are not limited to, predictable suppleness, flexibility, uniform pliability sufficient to stretch and expand without tearing during tissue expansion (i.e., using a breast implant and/or tissue expander), sufficient tensile strength for breast reconstruction and other plastic surgery applications, improved handling properties, and substantially uniform porosity that promotes rapid and efficient cellular ingrowth equally from either side of the ACDM.

In one embodiment of the invention, an ACDM is derived from allograft dermal tissue that is recovered from deeper within the dermis, and is therefore farther from, and not adjacent the epidermis. The procedure for preparing such an ACDM according to one embodiment of the invention is described below.

Figure 1:
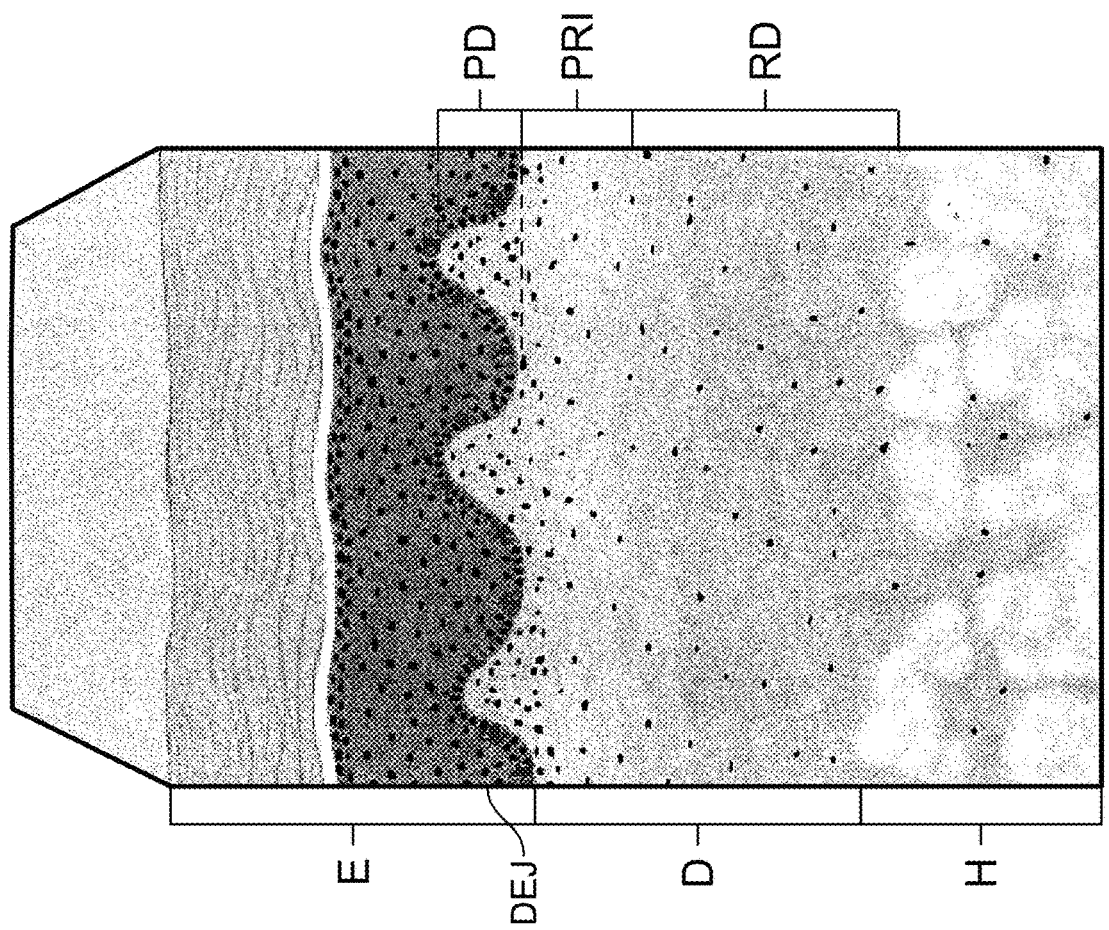
FIG. 1 is a perspective schematic view of a section of human skin and the various components thereof.
Figure 2:
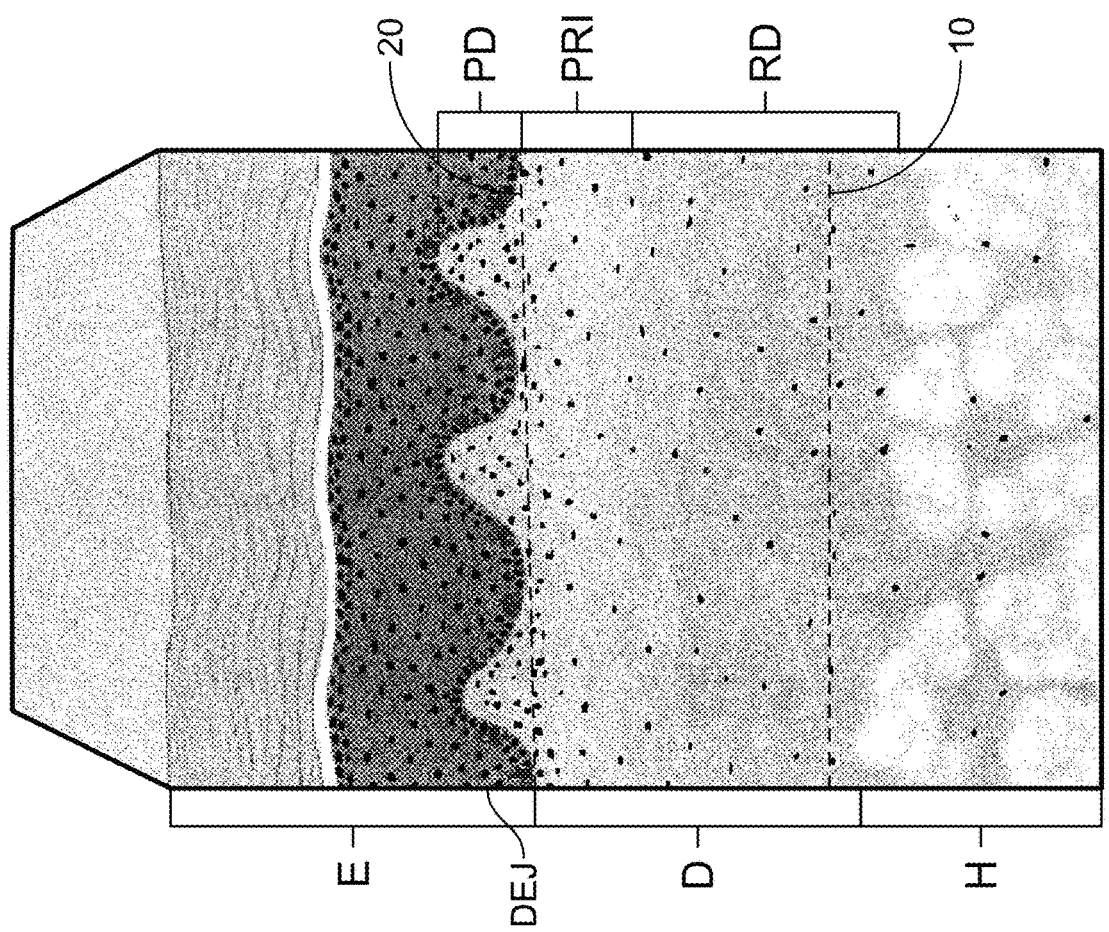
FIG. 2 is perspective schematic view of the section of human skin shown in FIG. 1, and also illustrates the cutting steps performed on same according to an embodiment of the present invention.

The recovery of portions of the dermis D from the skin may be accomplished by various techniques and devices, such as, for example, a manual dermatome technique, or dissection with a scalpel. In an embodiment illustrated in FIG. 2, a first cut 10 is made into the reticular dermis RD of the skin (e.g., a section of skin cut from the entire donor skin) proximate the underlying hypodermis H in order to remove it from the dermis D. A second cut 20 is then made into the epidermal portion of the papillary dermis PD containing the dense collagen matrix, as discussed in the foregoing Background section, in order to remove the epidermis E, the DEJ, and the underlying epidermal portion of the papillary dermis PD. The remaining portion of the dermis D (i.e., the deeper dermal portion of the papillary dermis PD and the reticular dermis RD) constitutes a collagen matrix having substantially uniform density and porosity.

In one embodiment, the remaining portion of the dermis ("the tissue") is then minimally processed, e.g., according to the process disclosed in U.S. Pat. No. 7,723,108, the disclosure of which is incorporated by reference herein in its entirety. In another embodiment, the tissue is decellularized by chemically treating it with saline, detergent, peracetic acid, ethanol and propylene glycol. The tissue is then washed with sterile water to remove residual processing chemicals. The disinfected and acellular tissue is cut into rectangular-shaped sheets suitable for clinical uses. The tissue sheets are treated with aqueous ethanol and then packaged to provide a hydrated collagen matrix, i.e., the ACDM.

The process(es) used to treat the tissue preserves the extracellular matrix of the dermis. The resulting ACDM thereby provides a framework to support cellular repopulation, vascularization, and tissue regeneration at the surgical site.

The ACDM derived using the process(es) disclosed above (referred to herein as the "Disclosed ACDM") exhibits properties that are ideal for its use as a sling in breast reconstruction, and its use in other plastic surgery applications, as is evident from the Examples presented below. Use of the Disclosed ACDM minimizes adhesions and foreign body reactions while promoting vascularization, cellular attachment, and tissue ingrowth at the surgical site. Compared to the prior art ACDMs (i.e., those discussed in the Background section), the Disclosed ACDM possesses more uniform tensile properties (i.e., strength, pliability, stretchability and handling characteristics) that are optimal for its use in breast reconstruction and other plastic surgery applications. The Disclosed ACDM also possesses improved suture retention strength, and elasticity and deformability that are optimal for its intended use. For example, the improved elasticity of the Disclosed ACDM promotes better expansion of the tissue in breast reconstruction. The Disclosed ACDM is therefore very strong and closely mimics the biomechanical properties of the tissue that it is intended to replace. Further, the Disclosed ACDM is resistant to bacterial colonization and non-immunogenic as a result of the treatment thereto and decellularization thereof.

FIGS. 3 and 4 illustrate use of the ACDM as a sling for breast reconstruction. As shown in these figures, the ACDM conforms to the shape of the breast implant (or tissue expander) in its function as a supportive sling.

Figure 5B:
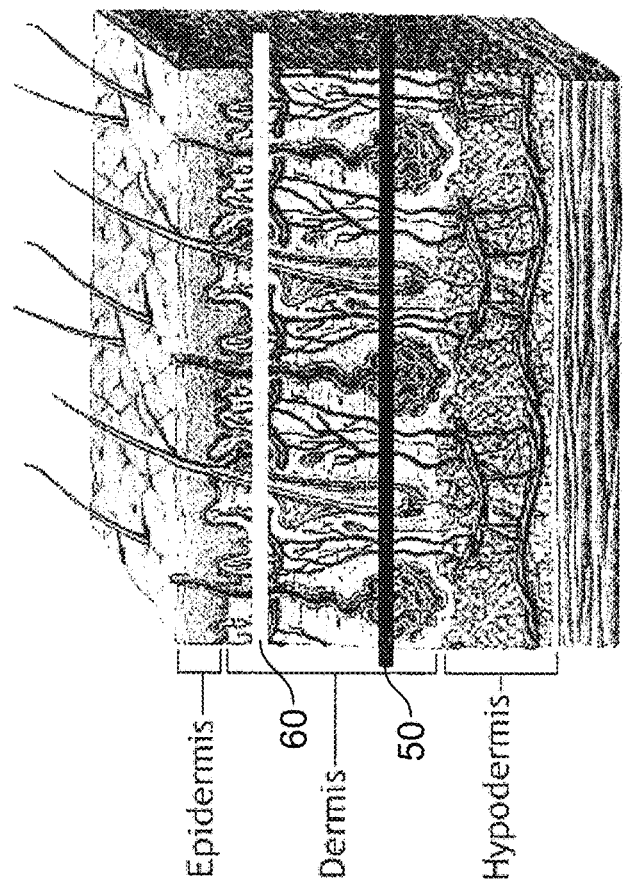
FIG. 5b is a perspective schematic view of a process according to an embodiment of the present invention, as performed on a section of human skin.
Figure 5A:
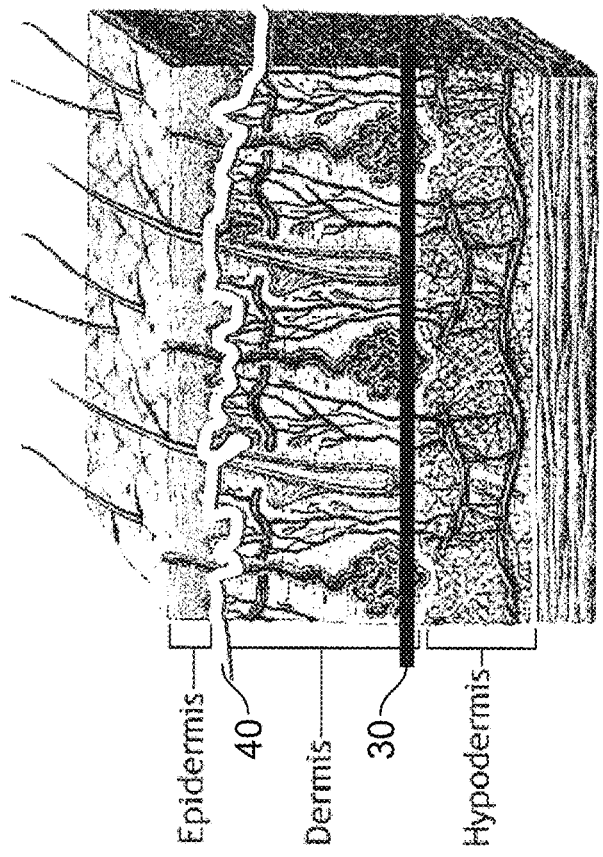
FIG. 5a is a perspective schematic view of a prior art process, as performed on a section of human skin.

FIG. 5a illustrates the process for fabricating the prior art ACDMs (i.e., the FlexHD® Structural™ ACDM, AlloDerm® ACDM and AlloDerm® RTU ACDM), namely, cutting the lower portion of the dermis and hypodermis (represented by straight line 30), and chemically treating the tissue to remove only the epidermis (represented by uneven line 40) and expose the DEJ.

FIG. 5b illustrates the process for fabricating the Disclosed ACDM according to an embodiment of the present invention. The lower portion of the dermis and hypodermis are cut (represented by straight line 50), and then a second cut (represented by straight line 60), is made deeper into the dermis than the chemical treatment used to fabricate the prior art ACDMs. In one embodiment, the second cut results in the removal of the epidermis, the DEJ, and the upper, epidermal portion of the papillary dermis.

Presented and discussed below are Examples that illustrate the comparative biomechanical properties of the Disclosed ACDM and the prior art ACDMs (i.e., the FlexHD® Structural™ ACDM, AlloDerm® ACDM and AlloDerm® RTU ACDM).

Example 1—In Vitro Fibroblast Attachment to the ACDMs

Materials and Methods 7 mm punches of each tissue sample (i.e., each ACDM) were prepared and seeded with $1 \times 10^5$ BJ neonatal human foreskin fibroblasts (ATCC, Manassa, Va.) on both sides in Eagles Minimum Essential Medium+10% fetal bovine serum. After 30 minutes, the tissue sections were washed to remove any non-adherent cells and incubated at 37° C. for 1 hour in complete growth medium. Attached cells were quantified using CyQuant Cell Proliferation Assay (Invitrogen, Carlsbad, Calif.) according to the manufacturer's instructions. Non-adherent seeded controls were measured for all samples. The test was replicated with each sample set. Values for cell fluorescence were reported. Tissue from multiple donor lots were collected, processed as described and tested. In addition, five lots of AlloDerm® RTU thick tissue were obtained and tested as commercial controls.

Results

TABLE 1

In vitro fibroblast attachment

|  | No. of Samples | Cells* | Grouping** |
|---|---|---|---|
| FlexHD Structural | | | |
| Dermis | 60 | 6047/242 | BC |
| Epidermis | 60 | 2620/270 | D |
| Disclosed ACDM | | | |
| Dermis | 77 | 8379/308 | A |
| Epidermis | 78 | 7246/359 | AB |
| AlloDerm | | | |
| Dermis | 42 | 4568/476 | C |
| Epidermis | 42 | 1548/379 | DE |
| AlloDerm RTU | | | |
| Dermis | 36 | 2028/259 | DE |
| Epidermis | 36 | 1039/278 | E |

*Data presented as fluorescence units: mean/standard error of the mean, SEM.
**Statistically similar groups as determined by the Bonferroni Method (95% Confidence); means that do not share a letter are statistically different.

Figure 6:
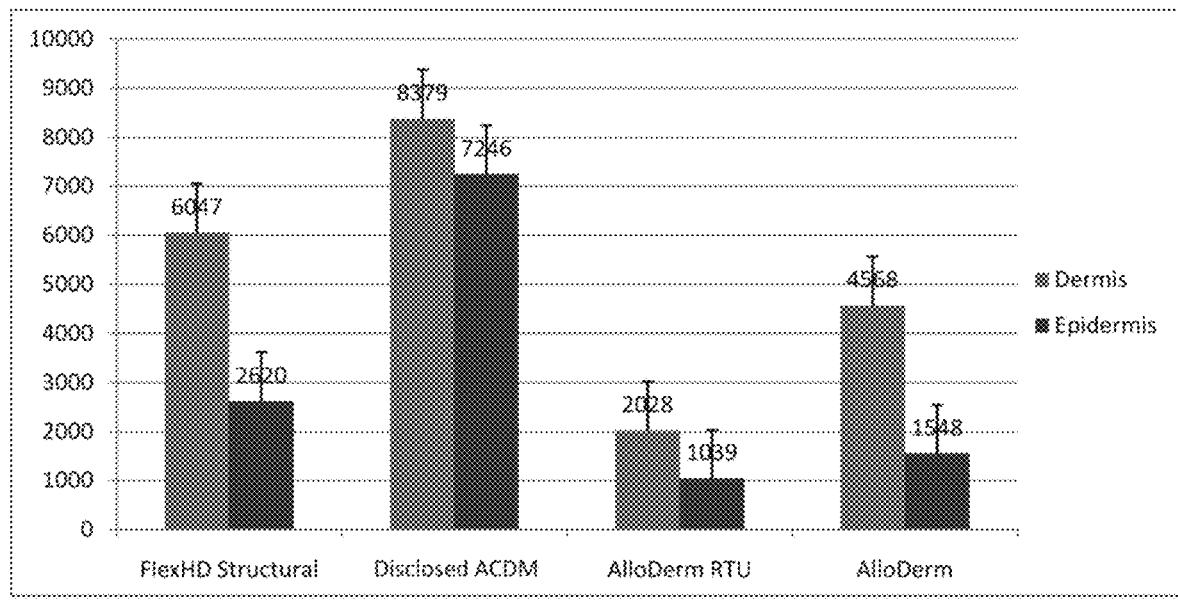
FIG. 6 is a graph of in vitro fibroblast attachment data for various ACDMs.

The results presented above are organized to show fibroblast attachment data for the dermis side and, separately, the epidermis side of each of the ACDMs. These results are similarly organized in the graph of FIG. 6 and the following discussion.

Dermal Side of Tissue:

The Disclosed ACDM had a statistically significant higher number of attached fibroblasts as compared to the FlexHD Structural ACDM; 8379 vs. 6047 fluorescence units. The AlloDerm ACDM had a greater number of attached fibroblasts as compared to the AlloDerm RTU ACDM; 4568 vs. 2028. It is noteworthy that the AlloDerm RTU ACDM had less than half as many attached fibroblasts as compared to the AlloDerm ACDM; this is a statistically significant difference. Finally, the number of attached fibroblasts for the Disclosed ACDM (8379) was much greater than for either the AlloDerm ACDM (4568) or AlloDerm RTU ACDM (2028). These differences are also statistically significant.

Epidermal Side of Tissue:

The Disclosed ACDM had a statistically significant higher number of attached fibroblasts as compared to the FlexHD Structural ACDM; 7246 vs. 2620 fluorescence units. The AlloDerm ACDM had roughly the same level of attached fibroblasts as the AlloDerm RTU ACDM; 1548 vs. 1039. These were much lower than for the FlexHD Structural ACDM or the Disclosed ACDM. Accordingly, the Disclosed ACDM had a much higher level of attached fibroblasts (7246) as compared to either the AlloDerm ACDM (1548) or the AlloDerm RTU ACDM (1039). The difference between the cell attachment level for the Disclosed ACDM is statistically significantly different than for either of the AlloDerm ACDM or the AlloDerm RTU ACDM.

Discussion

The Disclosed ACDM is derived from a deeper cut into the dermis layer relative to the source of the FlexHD Structural ACDM (see, e.g., FIGS. 5a and 5b). The porosity of this tissue increases with increased depth into the dermis. Accordingly, the interconnected channels are larger. As a corollary, the pores are more uniform at the two surfaces of a deep cut dermis.

In Table 1, the data show that the deeper cut Disclosed ACDM has many more attached fibroblasts than the FlexHD Structural ACDM. Also, the in vitro fibroblast attachment is clearly different for the two sides, dermis and epidermis, of the FlexHD Structural ACDM. For the deeper cut Disclosed ACDM, the in vitro fibroblast attachment is more equal for the two sides.

Both the AlloDerm and AlloDerm RTU ACDMs have much lower numbers of attached fibroblasts than do either the Disclosed ACDM or the FlexHD Structural ACDM. The Disclosed ACDM actually has a 76% higher frequency of fibroblast attachment compared to that of the AlloDerm RTU ACDM. The AlloDerm RTU ACDM has a 56% lower frequency of cell attachment than that of the AlloDerm ACDM.

Example 2—Tensile Properties of the ACDMs

Materials and Methods

Tissue samples (i.e., for each ACDM) were tested on an MTS 858 Mini Bionix System. Sample thickness was first measured with a laser micrometer (Z Mike, Benchmike 4050S). Samples in dogbone configuration (1 cm×7 cm; ASTM 638) were positioned in pneumatic action grips set at 29 psi pressure at a gage length of 26 mm. Tissue was pulled to break at a strain rate of 50.6 mm/min. Ultimate tensile strength, elongation-at-break and elastic modulus were recorded. Statistical analysis included both tests of the means and the estimates of variability for tensile strength, elongation-at-break, and modulus.

Results

As a result of the more open structure and greater porosity of the Disclosed ACDM, as contrasted with the FlexHD Structural ACDM, the Disclosed ACDM has reduced tensile strength as compared to the FlexHD Structural ACDM; 10.97 vs. 15.36 MPa.

Figure 7:
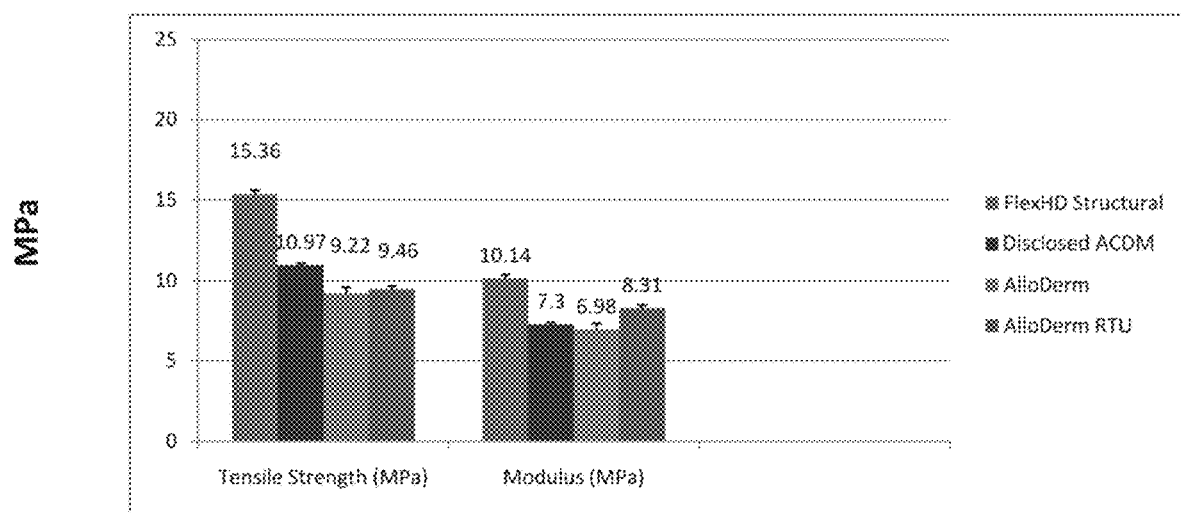
FIG. 7 is a group of graphs of tensile property data for various ACDMs.
Figure 7:
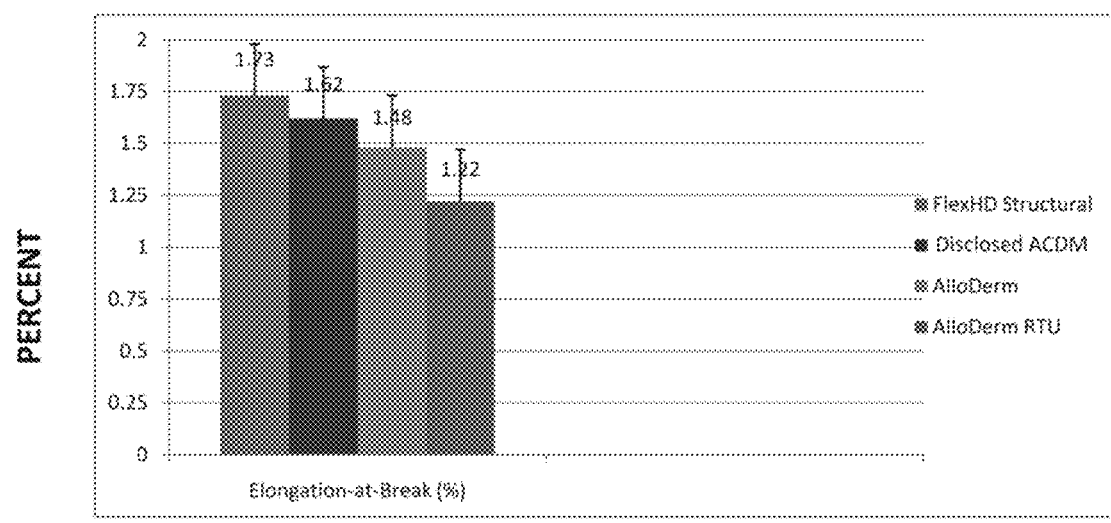

As can be seen from the data in Table 2 and the graph illustrated in FIG. 7, the Disclosed ACDM had a tensile strength higher than that of both the AlloDerm and AlloDerm RTU ACDMs; (10.97 vs. 9.22 and 9.46 MPa, respectively). These differences are statistically significant.

Modulus is a measure of flexibility. In other words, the greater its modulus, the more stiffness a material exhibits. The modulus of the Disclosed ACDM was 38% lower (and therefore less stiff) than that of the FlexHD Structural ACDM; 7.30 vs. 10.14 MPa (see the graph illustrated in FIG. 7). This difference is statistically significant.

The modulus of the Disclosed ACDM is statistically equivalent to that of the AlloDerm ACDM; 7.30 vs. 6.98 MPa (see the graph illustrated in FIG. 7). The AlloDerm RTU ACDM was, however, less flexible than either the AlloDerm ACDM or the Disclosed ACDM; 8.31 vs. 6.98 or 7.30 MPa. These differences are statistically significant. Based on the modulus results, the AlloDerm RTU ACDM was 19% stiffer than the AlloDerm ACDM. This difference is statistically significant.

Elongation-at-break is a measure of the amount of stretch before tensile failure. For this parameter, the Disclosed ACDM and the AlloDerm ACDM were statistically equivalent; 1.73 vs. 1.62 mm/mm. The AlloDerm RTU ACDM, however, had a statistically lower elongation-at-break as compared to either the Disclosed ACDM or the AlloDerm ACDM; 1.22 mm/mm vs. 1.73 or 1.48 mm/mm.

TABLE 2

TENSILE PROPERTIES*
DERMAL TISSUES FOR PLASTIC SURGERY

| TISSUE | NO. OF DONORS | NO. OF SAMPLES | ULTIMATE TENSILE STRENGTH mean/SEM (MPa) | Grouping** | MODULUS mean/SEM (MPa) | Grouping | ELONGATION-AT-BREAK mean/SEM (%) | Grouping |
|---|---|---|---|---|---|---|---|---|
| Flex HD Structural | 5 | 154 | 15.36/0.34 | A | 10.14/0.25 | A | 1.73/0.04 | A |
| Disclosed ACDM | 6 | 300 | 10.97/0.21 | B | 7.30/0.13 | C | 1.62/0.02 | AB |
| Alloderm | 11 | 88 | 9.22/0.54 | C | 6.98/0.38 | C | 1.48/0.05 | B |
| Alloderm RTU | 6 | 100 | 9.46/0.22 | C | 8.31/0.22 | B | 1.22/0.02 | C |

*Data presented as mean/standard error of the mean, SEM.

**Statistically similar groups as determined by the Bonferroni Method (95% Confidence); means that do not share a letter are statistically different.

Discussion

Since the porosity of the tissue in the Disclosed ACDM is significantly greater than that of the FlexHD Structural ACDM, the tensile properties were expected to be different; this difference was confirmed. The Modulus, a measure of flexibility, was 38% lower, i.e., more flexible for the deeper cut Disclosed ACDM relative to the FlexHD Structural ACDM. Also, the Disclosed ACDM had a higher level of flexibility (13.8%) relative to the AlloDerm RTU ACDM.

The stretchability of these tissues may be expressed in terms of the elongation-at-break data. The stretchability of the Disclosed ACDM and the AlloDerm ACDM were equivalent. However, the stretchability of the Disclosed ACDM by this measure is 33% higher relative to the AlloDerm RTU ACDM.

An expected decrease in tensile strength of 29% was observed in the Disclosed ACDM, relative to that of the FlexHD Structural ACDM. It is noteworthy that the tensile strength of the Disclosed ACDM was 40% greater than for the AlloDerm ACDM and 39% greater than for the AlloDerm RTU ACDM.

Example 3—Surface Characterization of the ACDMs by Scanning Electron Microscopy (SEM)

Materials and Methods

Tissue samples (i.e., for the Disclosed ACDM and the FlexHD Structural ACDM) were lyophilized and coated with a 10 nm layer of gold. Images were taken using a Field Emission Zeiss Scanning Microscope (Carl Zeiss, Inc., Thornwood, N.Y.) with a working distance of 5-10 mm and voltage range of 30-200 kV. All images were taken at the Department of Ceramics and Material Science at Rutgers University, New Brunswick, N.J.

Results

Figure 8A:
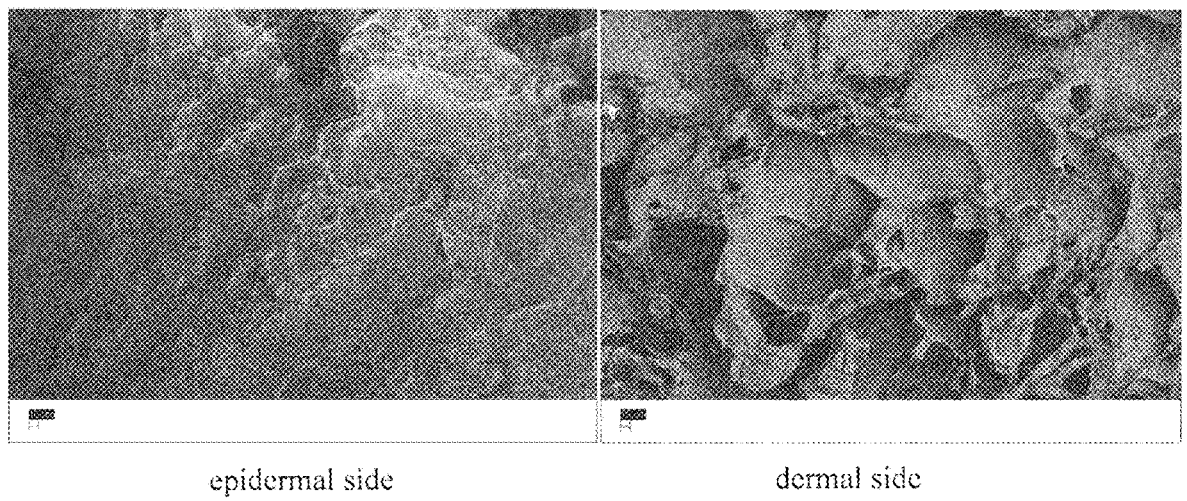
FIGS. 8a and 8b are scanning electron micrographs of various ACDMs.
Figure 8B:
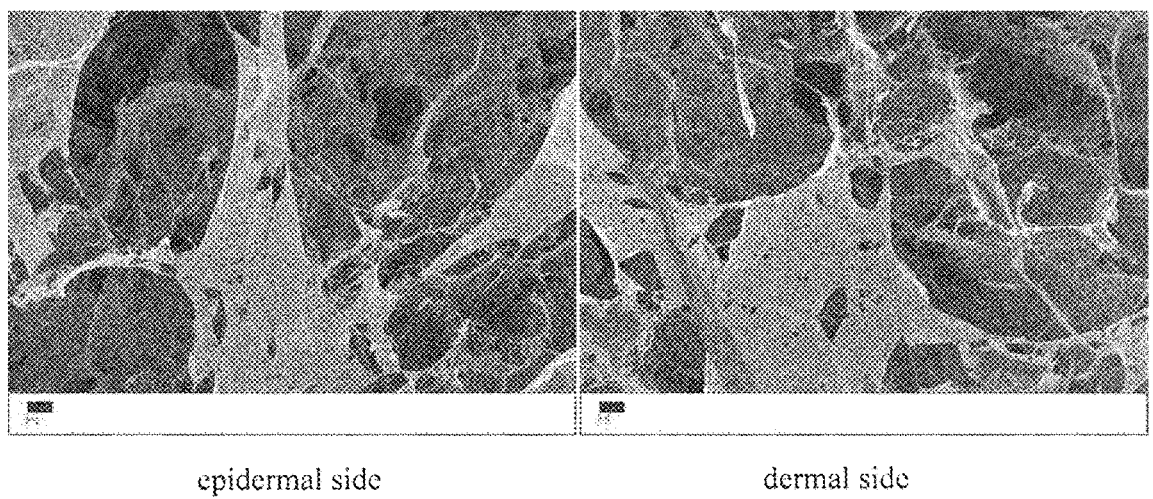

Scanning electron micrographs of the epidermal side and the dermal side of both the FlexHD Structural ACDM and the Disclosed ACDM are presented in FIGS. 8a and 8b, respectively. Representative images were taken at 250× for all samples. For both ACDMs, the micrographs of the epidermal side of the ACDMs are shown on the left, and the micrographs of the dermal side are shown on the right.

Discussion

The deeper cut method of the present invention that was used to derive the Disclosed ACDM results in a different microstructure as compared to that of the FlexHD Structural ACDM. In contrast to the FlexHD Structural ACDM, the SEM images clearly show the more open and porous structure of the Disclosed ACDM. The dermal and epidermal sides are very similar for the Disclosed ACDM.

Example 4—Surface Appearance of the ACDMs by Histology (Hematoxylin & Eosin Staining)

Materials and Methods

Tissue sections (i.e., for the Disclosed ACDM and the FlexHD Structural ACDM) were fixed in 10% neutral buffered formalin prior to paraffin embedding, sectioned and stained via hematoxillin and eosin (H & E). All histological processing was performed at Premier Laboratory (Longmont, Colo.). Imaging was also performed at Premier using AperioScope software (Vista, Calif.). Representative images were taken at 10× magnifications.

Results

Figure 9A:
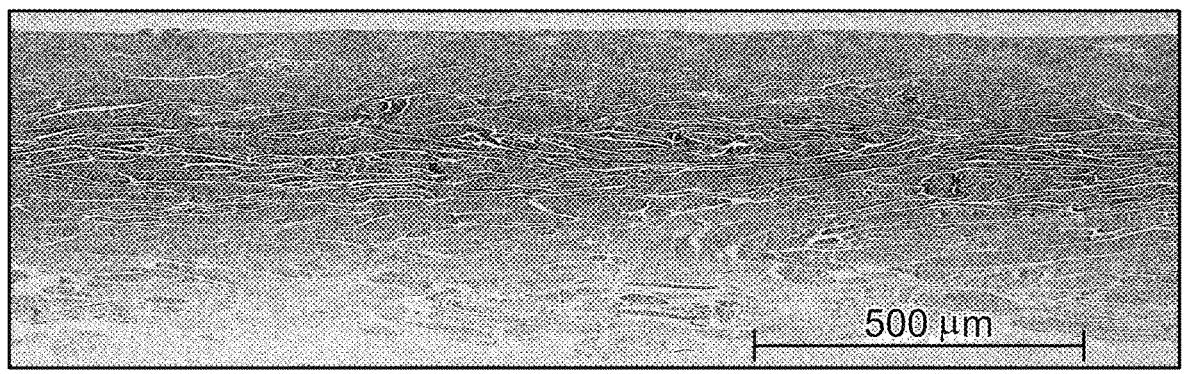
FIGS. 9a and 9b are histological images of various ACDMs.
Figure 9B:
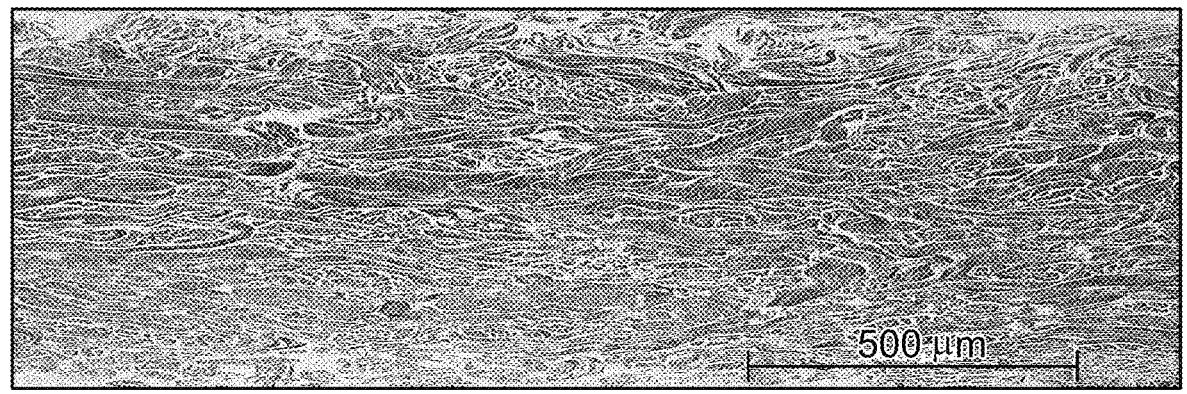

Images of the stained FlexHD Structural ACDM and the Disclosed ACDM are presented in FIGS. 9a and 9b, respectively. The images are low magnification (10×) representative scans of the entire thickness of the tissue samples. In all images, the epidermal side is on the upper part of the scan. However, it should be noted that orientation for these samples was not maintained throughout histological processing. In some cases, the samples are virtually symmetrical through the thickness and when possible, macrostructural landmarks (such as presence of adipose or hair follicles) were used to identify sidedness.

As expected and illustrated in FIG. 9a, the FlexHD Structural ACDM shows a dense structure with an even topography on the epidermal side. Towards the dermal side, the structure becomes less dense, with the tissue directly adjacent to the cut edge showing high fragmentation. On the other hand, FIG. 9b shows that the Disclosed ACDM possesses a more uniform collagen matrix with no distinguishable differences between the epidermal and dermal sides.

Discussion

The histology images are consistent with the SEM images of FIGS. 8a and 8b, showing the similarity of the dermal and epidermal sides of the Disclosed ACDM. Based on the results in Examples 3 and 4, the Disclosed ACDM will cause relatively less confusion and concern about identifying and maintaining the side orientation thereof, when compared to FlexHD Structural ACDM and other ACDMs.

Example 5—Suture Retention Strength Testing of the ACDMs

Materials and Methods

A size 0 PDS® II suture with a 40 mm, ½ circle tapered needle (Ethicon, Inc., Somerville, N.J.) was placed 5 mm from the edge of 6 cm×1 cm test samples of the Disclosed ACDM, the FlexHD Structural ACDM and the AlloDerm ACDM. With one end of the sample fixed, the suture was pulled through the material of the sample until failure. The load at failure was recorded on a MTS Mini Bionix System.

Results

TABLE 3

| | Suture Retention* | | | |
|---|---|---|---|---|
| ACDM Sample | No. of Donors | No. of Samples | Suture Retention Strength (MPa) Mean/SEM | Grouping** |
| FlexHD Structural ACDM | 40 | 709 | 3.40/0.03 | B |
| Disclosed ACDM | 9 | 214 | 4.10/0.07 | A |
| AlloDerm ACDM | 10 | 121 | 3.20/0.9 | B |

*Data presented as mean/standard error of the mean, SEM.
**Statistically, similar groups as determined by the Bonferroni Method (95% Confidence); means that do not share a letter are statistically different.

Figure 10:
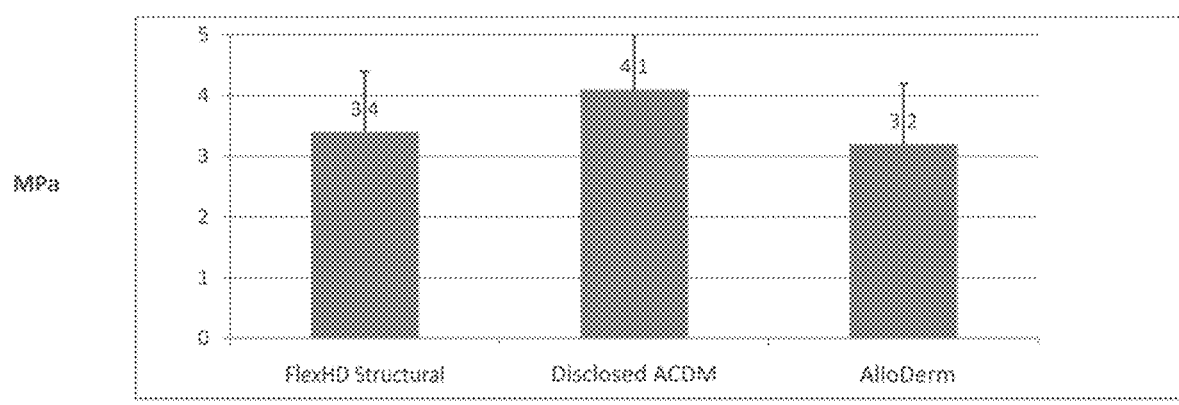
FIG. 10 is a graph of suture retention strength data for various ACDMs.

The ability of the Disclosed ACDM to be sutured without tearing (i.e., its suture retention strength) is statistically significantly higher than that for the AlloDerm ACDM and the FlexHD Structural ACDM (4.1 vs. 3.2 MPa and 4.1 vs. 3.4 MPa, respectively). The suture retention strengths of the AlloDerm ACDM and the FlexHD Structural ACDM were similar, and equivalent statistically. These results also presented in the graph of FIG. 10 and further discussed below.

Discussion

The ability of the Disclosed ACDM to resist tearing under load applied to the suture demonstrates that the Disclosed ACDM has somewhat higher suture pull-out values than that of the FlexHD Structural and AlloDerm ACDMs.

The higher suture retention strength of the Disclosed ACDM may be attributed to its increased flexibility arising from its more open, porous structure. The resilience provided by this "open net" structure could account for the higher suture retention strength.

Example 6—Variability of Tensile Properties of the ACDMs

Materials and Methods

A comparison of the variability of tensile properties was made between the Disclosed ACDM and the AlloDerm ACDM.

Statistical analyses were made of the standard deviations of the means for each tensile parameter: Ultimate tensile strength, Modulus, and Elongation-at-break. The standard deviations were compared using two independent statistical methods, F-test and Levine's test.

Statistical differences in the variability of the mean is established by two independent statistical methods. The standard F-Test demonstrates a very high statistically different level of variability in the tensile data with a p-value of 0.000. In addition, as a test for data with non-uniform distribution, the Levine test again demonstrates differences in the data variability at a statistically significant level with a p-value of 0.016.

Results

Figure 11A:
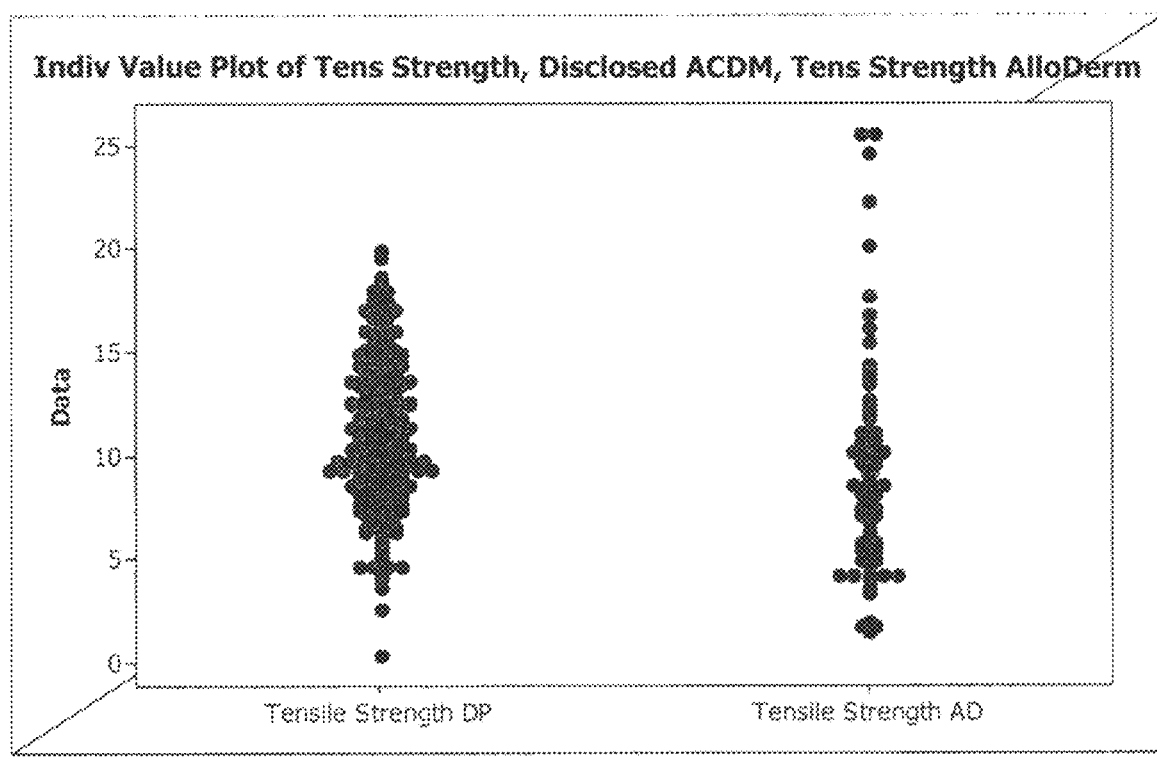
FIG. 11a is a plot of standard deviations in the tensile strength data for various ACDMs.
Figure 11B:
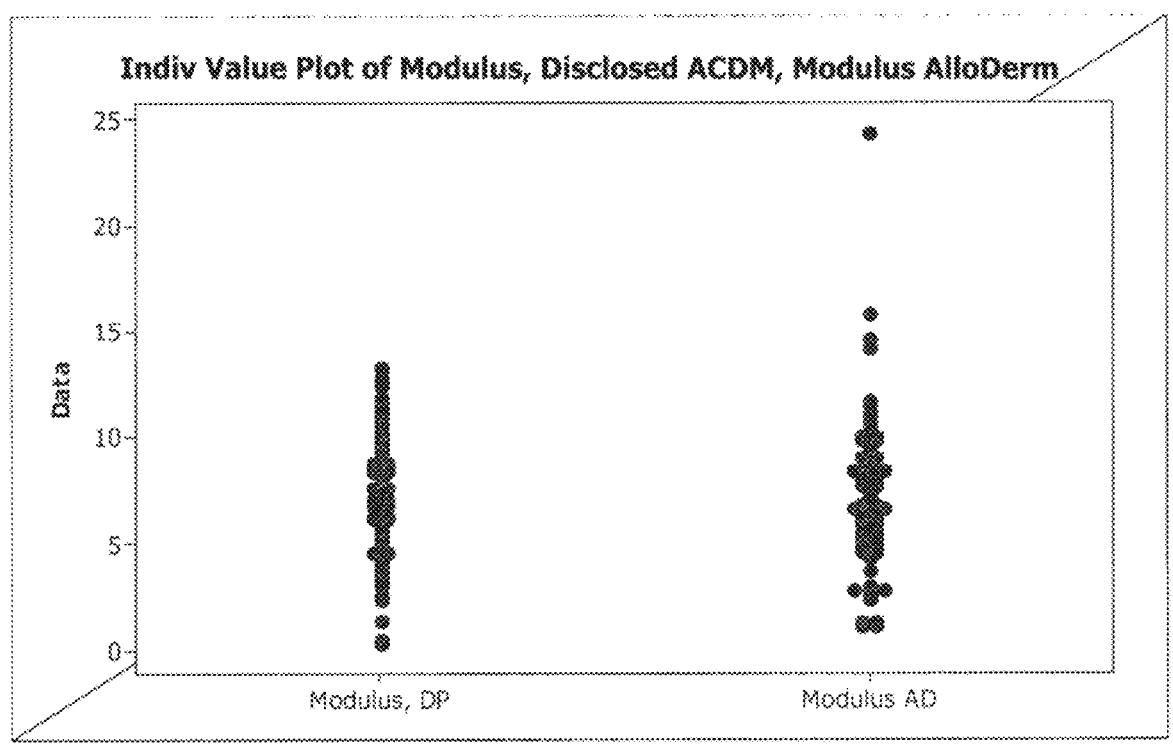
FIG. 11b is a plot of standard deviations in the modulus data for various ACDMs.
Figure 11C:
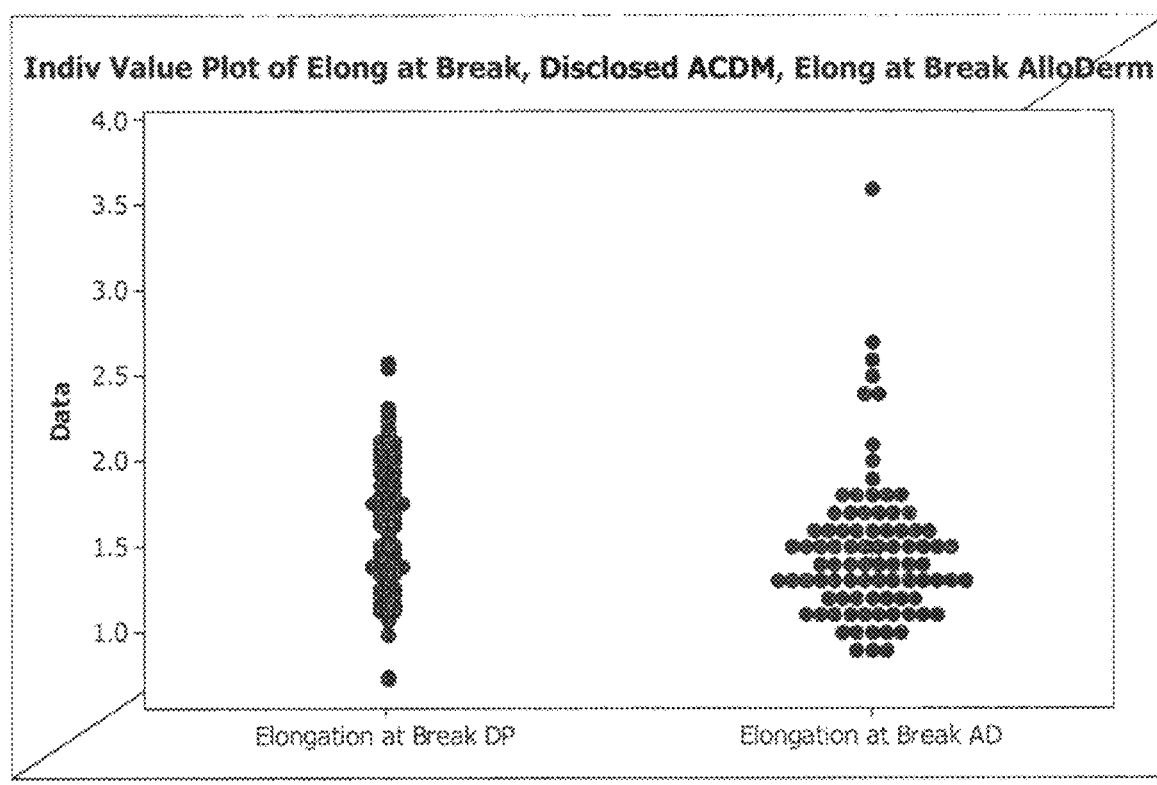
FIG. 11c is a plot of standard deviations in the elongation-at-break data for various ACDMs.

The data and results of the statistical analyses are presented in Table 4 and FIGS. 11a, 11b and 11c.

For Ultimate Tensile Strength (see FIG. 11a), the standard deviation for the Disclosed ACDM ("DP", left side) was statistically significantly lower than that of the AlloDerm ACDM ("AD", right side); 3.557 vs. 5.076. The statistical difference was valid for both statistical methods used.

For Modulus (see FIG. 11b), the standard deviation for the Disclosed ACDM ("DP", left side) was statistically significantly lower than that of the AlloDerm ACDM ("AD", right side); 2.260 vs. 3.532. The statistical difference was valid for both statistical methods used.

For Elongation-at-break (see FIG. 11c), the standard deviation of the Disclosed ACDM ("DP", left side) was statistically significantly lower than that of the AlloDerm ACDM ("AD", right side); 0.33 vs. 0.43. The statistical difference was valid utilizing the F-test.

The more uniform tensile properties of the Disclosed ACDM relative to those of the AlloDerm ACDM can readily be seen in the plots of individual values for the three tensile parameters, as shown in FIGS. 11a, 11b and 11c.

tensile properties between the Disclosed ACDM and the AlloDerm ACDM there is, however, a very significant difference in the variability of the tensile properties for these two dermal matrices. For all three tensile properties measured (i.e., tensile strength, modulus and elongation-to-break), the Disclosed ACDM exhibits a statistically lower variability of the tensile values than the AlloDerm ACDM. This results in greatly improved uniformity of handling properties among individual pieces. Consequently, the Disclosed ACDM is a more predictable tissue form.

To summarize the findings of the above Examples, the process for forming the Disclosed ACDM minimizes foreign body reactions while promoting vascularization, cellular attachment, and tissue ingrowth. The Disclosed ACDM becomes well incorporated into the surrounding tissues while avoiding adhesions. Tensile properties (strength, pliability and handling characteristics) of the Disclosed ACDM are optimized. Suture retention strength and uniformity of tensile properties are also significantly improved for the Disclosed ACDM. The Disclosed ACDM is very strong and closely mimic the biomechanical properties of the tissue that it is intended to replace. The Disclose ACDM maintains an optimal elasticity and deformability suited for the intended use, e.g., as a sling for use with breast implants and/or tissue expanders in breast reconstruction surgery.

Another allograft tissue form may be simultaneously derived using the process disclosed above in connection with the Disclosed ACDM. More particularly, an allograft tissue form is derived by the first cut made 10 into the reticular dermis RD of the skin to remove the underlying hypodermis H, as discussed above and illustrated in FIG. 2. The cut portion of the reticular dermis RD remains attached to the underlying hypodermis H, and therefore constitutes a "hybrid bilayer" tissue form that includes both a dermal side and an adipose (i.e., fat) tissue side. Such a tissue form is useful in surgical procedures in which both dermis and adipose tissue are required or desired, as the two tissues may serve different functions (e.g., a repair function and a bulking function, respectively). One example of such a surgical procedure is breast reconstructive surgery. Other examples may include various plastic, cosmetic and/or reconstructive surgeries.

It will be understood that the embodiments described herein are merely exemplary and that a person of ordinary skill in the art may make many variations and modifications without departing from the spirit and scope of the invention. All such variations and modifications are intended to be

TABLE 4

VARIABILITY OF TENSILE PROPERTIES

| | Tensile Strength | | Modulus | | Elongation-at-Break | |
|---|---|---|---|---|---|---|
| | Disclosed ACDM | Alloderm | Disclosed ACDM | Alloderm | Disclosed ACDM | Alloderm |
| Standard Deviation | 3.557 | 5.076 | 2.260 | 3.532 | 0.334 | 0.434 |
| Sample Size # Donors/# Samples | 5/300 | 11/87 | 5/300 | 11/87 | 5/300 | 11/88 |
| Stastically Significant F-Test | YES | | YES | | YES | |
| Levine's Test | YES | | YES | | NO* | |

*Data for Alloderm Elongation-At-Break is abnormally distributed.

Discussion

Variability of the tensile properties is much less for the Disclosed ACDM as compared to the Alloderm ACDM. While there appears to be a small difference in the actual included within the scope of the invention, and the appended claims. Some of the possible variations and modifications of the Disclosed ACDM and the dermis/adipose hybrid bilayer tissue form are disclosed below.

The Disclosed ACDM may be provided in particulated form in one embodiment, depending on the intended surgical use. The dermis/adipose hybrid bilayer tissue form may also be provided in particulated form in one embodiment. In other embodiments, the particulated Disclosed ACDM and/or particulated dermis/adipose bilayer hybrid tissue form may be combined with a carrier, and thereby constitute a flowable tissue form.

In other embodiments, the Disclosed ACDM may be provided in perforated or meshed form. Perforating the Disclosed ACDM or forming a mesh of the Disclosed ACDM makes it more porous, and ideal for certain surgical applications. The dermis/adipose hybrid bilayer tissue form may also be provided in perforated or meshed form in other embodiments.

In other embodiments, cells may be added to the Disclosed ACDM. Cells may also be added to the dermis/adipose hybrid bilayer tissue form. Such cells may include, for example, stem cells (e.g., embryonic stem cells, mesenchymal stem cells, adult stem cells, skin-derived stem cells, and amnion-derived stem cells), fibroblasts, osteoblasts, myoblasts, and keratinocytes.

In other embodiments, biological substances may be added to the Disclosed ACDM. Biological substances may also be added to the dermis/adipose hybrid bilayer tissue form. Such biological substances may include, for example, platelet-rich plasma ("PRP"), bone marrow aspirate, and/or demineralized bone particles or fibers and/or other allograft tissue forms. Further, amnion tissue (with or without the native cells thereof) may be added to the Disclosed ACDM and/or the dermis/adipose hybrid bilayer tissue form, e.g., to function as an anti-adhesion membrane.

In other embodiments, the Disclosed ACDM may be used to wrap around the above-identified biological substances or other biological substances. In such a wrapper function, the Disclosed ACDM may protect, enclose, and or insulate such biological substances upon implantation. The dermis/adipose hybrid bilayer tissue form may also be used as a wrapper for biological substances.

In other embodiments, reinforcing elements may be added to the Disclosed ACDM. Reinforcing elements may also be added to the dermis/adipose bilayer tissue form. Examples of such reinforcing elements include absorbable fibers and non-absorbable fibers. The reinforcing elements may be arranged in various patterns, such as, for example, a grid pattern.

In other embodiments, the Disclosed ACDM may be chemically modified to imbue it with enhanced properties. One example is cross-linking the collagen of the Disclosed ACDM. The dermis/adipose hybrid bilayer tissue form may also be chemically modified.

We claim:

1. A method for forming an allograft hybrid bilayer tissue form, comprising the steps of: (1) providing a donor tissue including a skin having (a) an epidermis; (b) a dermis underlying the epidermis, the dermis including a papillary dermis adjacent the epidermis, a reticular dermis distal to the epidermis, and a papillary-reticular dermis interface between the papillary dermis and reticular dermis; and (c) at least a portion of a hypodermis adipose tissue underlying the reticular dermis of (b) the dermis; (2) making a cut into the reticular dermis at a location proximate the hypodermis, and along a plane substantially parallel to the papillary-reticular dermis interface; and (3) removing and retaining at least a portion of the hypodermis adipose tissue and a portion of the reticular dermis attached to the hypodermis adipose tissue to form said allograft hybrid bilayer tissue form such that said allograft hybrid bilayer tissue form includes both a dermal side which is formed by the portion of the reticular dermis, and an adipose side which is formed by said at least a portion of the hypodermis adipose tissue.

2. The method of claim 1, further comprising the step of adding cells to the allograft hybrid bilayer tissue form.

3. The method of claim 1, further comprising the step of adding one or more biological s substances to the allograft hybrid bilayer tissue form.

4. The method of claim 1, further comprising the step of adding one or more reinforcing elements to the allograft hybrid bilayer tissue form.

5. The method of claim 1, further comprising the step of chemically modifying the allograft hybrid bilayer tissue form.

6. An allograft hybrid bilayer tissue form for use in surgical procedures comprising a dermal side and an adipose side, wherein said allograft hybrid layer tissue form is derived from a donor skin tissue which comprised (a) an epidermis; (b) a dermis underlying the epidermis, the dermis including a papillary dermis adjacent the epidermis, a reticular dermis distal to the epidermis, and a papillary-reticular dermis interface between the papillary dermis and reticular dermis; and (c) at least a portion of a hypodermis adipose tissue underlying the reticular dermis of (b) the dermis, wherein the dermal side of said tissue form is formed by a portion of the reticular dermis and the adipose side of said tissue form is formed by said at least a portion of hypodermis, and wherein the allograft hybrid bilayer tissue form essentially lacks an epidermis, a papillary dermis, papillary-reticular dermis interface, and a portion of the reticular dermis attached to the papillary- reticular dermis interface.

7. The allograft hybrid bilayer tissue form of claim 6, wherein said allograft hybrid bilayer tissue form is in particulate form.

8. The allograft hybrid bilayer tissue form of claim 6, wherein said allograft hybrid bilayer tissue form is perforated.

9. The allograft hybrid bilayer tissue form of claim 6, wherein said allograft hybrid bilayer tissue form is in mesh form.

10. The allograft hybrid bilayer tissue form of claim 6, further comprising cells.

11. The allograft hybrid bilayer tissue form of claim 10, wherein said cells include one or more of the group consisting of stem cells, fibroblasts, osteoblasts, myoblasts and keratinocytes.

12. The allograft hybrid bilayer tissue form of claim 6, further comprising one or more biological substances.

13. The allograft hybrid bilayer tissue form of claim 12, wherein said one or more biological substances are selected from the group consisting of platelet-rich plasma, bone marrow aspirate, and other allograft tissue forms.

14. The allograft hybrid bilayer tissue form of claim 6, further comprising reinforcing elements.

15. The allograft hybrid bilayer tissue form of claim 14, wherein said reinforcing elements are absorbable fibers.

16. The allograft hybrid bilayer tissue form of claim 14, wherein said reinforcing elements are non-absorbable fibers.

* * * * *